United States Patent [19]

Buchecker et al.

[11] Patent Number: 5,185,098

[45] Date of Patent: Feb. 9, 1993

[54] LIQUID CRYSTALLINE MIXTURES CONTAINING 3,4-DIFLUOROPHENYL-SUBSTITUTED BICYCLOHEXYLS

[75] Inventors: Richard Buchecker, Zürich; Martin Schadt, Seltisberg; Alois Villiger, Basel, all of Switzerland

[73] Assignee: Hoffmann-La Roche Inc., Nutley, N.J.

[21] Appl. No.: 505,197

[22] Filed: Apr. 5, 1990

[51] Int. Cl.[5] .................. C09K 19/30; C07C 19/08
[52] U.S. Cl. .................. 252/299.63; 570/128; 359/102
[58] Field of Search .......... 252/299.01, 299.63; 570/128; 359/102

[56] References Cited

U.S. PATENT DOCUMENTS

| | | | |
|---|---|---|---|
| 4,405,488 | 9/1983 | Sugimori et al. | 252/299.63 |
| 4,629,581 | 12/1986 | Petrzilka et al. | 252/299.63 |
| 4,654,421 | 3/1987 | Tanaka et al. | 252/299.63 X |
| 4,676,604 | 6/1987 | Petrzilka et al. | 350/350 R |
| 4,710,315 | 12/1987 | Schad et al. | 252/299.63 |
| 4,770,503 | 9/1988 | Buchecker et al. | 350/350 R |
| 4,797,228 | 1/1989 | Goto et al. | 252/299.63 |
| 4,814,523 | 3/1989 | Tanaka et al. | 252/299.63 X |
| 4,820,443 | 4/1989 | Goto et al. | 252/299.63 X |
| 4,822,519 | 4/1989 | Saito et al. | 252/299.63 X |
| 4,886,621 | 12/1989 | Sage et al. | 252/299.63 X |
| 4,910,350 | 3/1990 | Tanaka et al. | 252/299.63 X |
| 4,917,819 | 4/1990 | Goto et al. | 252/299.63 |
| 4,923,632 | 5/1990 | Sawada et al. | 252/299.63 |
| 4,946,986 | 8/1990 | Tanaka et al. | 252/299.63 |
| 5,122,295 | 6/1992 | Weber et al. | 252/299.63 |

FOREIGN PATENT DOCUMENTS

| | | | |
|---|---|---|---|
| 205998 | 12/1986 | European Pat. Off. | 252/299.63 |
| 258868 | 3/1988 | European Pat. Off. | 252/299.63 |
| 315014 | 5/1989 | European Pat. Off. | |
| 316186 | 5/1989 | European Pat. Off. | 252/299.63 |
| 318003 | 5/1989 | European Pat. Off. | 252/299.63 |
| 3139130 | 5/1982 | Fed. Rep. of Germany | 252/299.63 |
| 3631611 | 4/1988 | Fed. Rep. of Germany | |
| 3736489 | 5/1989 | Fed. Rep. of Germany | 252/299.63 |

OTHER PUBLICATIONS

Schadt, M. et al. Liq. Cryst. 7(4) 519 1990.
Derwent 88-099224/15.
Derwent 82-37527 E/19 (1982).
Schadt, Program of "The 8th Liquid Crystal Conference of Socialistic Countries" Slides, Abstracts, Krakow, Poland, Aug. 28–Sep. 1, 1989.
Slides of Dr. Schadt presented at "The 8th Liquid Crystal Conference of Socialistic Countries", Krakow, Poland, Aug. 28–Sep. 1, 1989.
Abstract of Dr. Schadt's presentation at "The 8th Liquid Crystal Conference of Socialistic Countries", Krakow, Poland, Aug. 28–Sep. 1, 1989.

Primary Examiner—Robert L. Stoll
Assistant Examiner—Philip Tucker
Attorney, Agent, or Firm—George M. Gould; William H. Epstein; John J. Schlager

[57] ABSTRACT

Compounds of formula

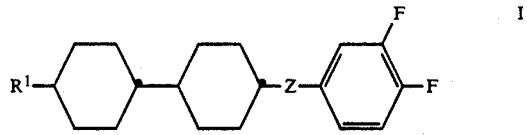

wherein Z is a single covalent bond or —$CH_2CH_2$—, and $R^1$ is 1E-alkenyl with 2–12 carbon atoms, liquid crystalline mixtures containing them and their use for electro-optical purposes.

14 Claims, No Drawings

LIQUID CRYSTALLINE MIXTURES CONTAINING 3,4-DIFLUOROPHENYL-SUBSTITUTED BICYCLOHEXYLS

FIELD OF THE INVENTION

The present invention is concerned with novel 3,4-difluorophenyl-substituted trans,trans-bicyclohexyls, liquid crystalline mixtures which contain such compounds as well as their use for electro-optical purposes.

BACKGROUND OF THE INVENTION

Liquid crystals are used primarily as dielectrics in indicating devices, since the optical properties of such substances can be influenced by an applied voltage. Electro-optical devices based on liquid crystals are well-known to the person skilled in the art and can be based on various effects. Examples of such devices are cells based on dynamic scattering, DAP cells (deformation of aligned phases), guest/host cells, and devices having a twisted nematic structure, such as TN cells (twisted nematic), STN cells (super-twisted nematic), SBE cells (super-birefringence effect) and OMI cells (optical mode interference). The most common indicating devices are based on the Schadt-Helfrich effect and have a twisted nematic structure.

The liquid crystal materials must have a good chemical and thermal stability and a good stability towards electric fields and electromagnetic radiation. Further, the liquid crystal materials should have a low viscosity and should give short response times, low threshold potentials and a high contrast in the cells. Furthermore, at usual operating temperatures from about $-30°$ C. to about $+80°$ C., especially from about -20° C. to about $+60°$ C., they should have a suitable mesophase, for example a nematic or cholesteric mesophase for the above-mentioned cells. Further properties such as the electrical conductivity, the dielectric anisotropy and the optical anisotropy must fulfill different requirements depending on the type of cell and field of application. For example, materials for cells having a twisted nematic structure should have a positive dielectric anisotropy and an electrical conductivity which is as low as possible. For some years there has been an increased interest in actively addressed liquid crystal devices, for example TFT applications (thin film transistor) in television sets. The use of cyano compounds with positive dielectric anisotropy in such devices, however, leads in most cases to an undesired increase in the electrical conductivity.

Since liquid crystals are generally used as mixtures of several components, it is important that the components have a good miscibility with one another.

SUMMARY OF THE INVENTION

The present invention provides compounds of the formula

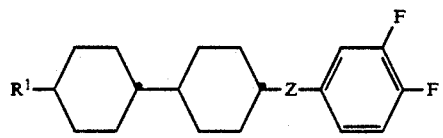

wherein Z is a single covalent bond or —CH$_2$CH$_2$—, and R$^1$ is 1E-alkenyl with 2-12 carbon atoms.

DETAILED DESCRIPTION OF THE INVENTION

The present invention provides compounds of the formula

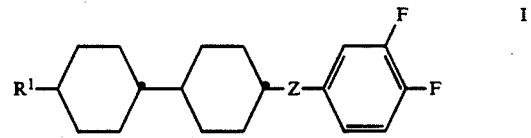

wherein Z is a single covalent bond or —CH$_2$CH$_2$—, and R$^1$ is 1E-alkenyl with 2-12 carbon atoms.

The compounds in accordance with the invention are liquid crystals with comparatively broad mesophase ranges and high clearing points. They possess low optical anisotropies and surprisingly low viscosities, in particular low rotational viscosities. They are well soluble in known liquid crystal materials. In spite of the relatively weak permanent dipole moments they possess surprisingly large positive dielectric anisotropies and enable low threshold and operating potentials. Moreover, they possess a high electrical resistance. Therefore, the compounds in accordance with the invention are particularly suitable to achieve simultaneously low threshold potentials and short response times.

The compounds in accordance with the invention can preferably be used as components of nematic or cholesteric mixtures. By virtue of their good solubility they can generally be used in high concentrations, if desired.

The above term "1E-alkenyl" embraces straight-chain and branched, chiral or non-chiral groups. The straight-chain groups vinyl, 1E-propenyl, 1E-butenyl, 1E-pentyl, 1E-hexenyl, 1E-heptenyl, 1E-octenyl, 1E-nonenyl, 1E-decenyl, 1E-undecenyl and 1E-dodecenyl generally are preferred. Group R$^1$ preferably has 2-7 carbon atoms, especially 2-5 carbon atoms.

The term "alkyl" means straight-chain and branched residues which preferably have 1 to 12 carbon atoms; and especially preferred are 1-7 carbon atoms.

The term "alkoxy" means a straight or branched chain hydrocarbonoxy group in which the "alkyl" portion is defined above, for example, methoxy, ethoxy, propoxy, and the like.

The term "3E-alkenyl" means straight-chain and branched residues which preferably have 4 to 12 carbon atoms, for example, 3-butenyl, 3E-pentenyl, 3E-hexenyl, 3E-heptenyl, and the like.

The term "4-alkenyl" means straight-chain and branched residues which preferably have 5 to 12 carbon atoms, for example, 4-pentenyl, 4-hexenyl, 4-heptenyl, and the like.

The term "2E-alkenyloxy" means straight-chain and branched residues which preferably have 3 to 12 carbon atoms, for example, allyloxy, 2E-butenyloxy, 2E-pentenyloxy, 2E-hexenyloxy, 2E-heptenyloxy, and the like.

The term "3-alkenyloxy" means straight-chain and branched residues which preferably have 4 to 12 carbon atoms, for example, 3-butenyloxy, 3-pentenyloxy, 3-hexenyloxy, 3-heptenyloxy, and the like.

In general, 3E-alkenyl, 4-alkenyl, 2E-alkenxloxy, and 3-alkenyloxy preferably mean straight-chain residues. Especially preferred are groups with up to 7 carbon atoms.

The compounds of formula I can be prepared in a manner known per se for example by reacting an aldehyde of the formula $$\text{OHC}-\left[\text{cyclohexyl}\right]-\left[\text{cyclohexyl}\right]-Z-\left[\text{phenyl}\right]\begin{array}{c}F\\F\end{array} \quad \text{II}$$

wherein Z has the above significances, with alkyltriphenylphosphonium halide in the presence of a base.

Preferred bases and reaction conditions as well as preferred methods for the isomerization of the double bond, if necessary, are known per se, for example from U.S. Pat. No. 4,676,604 incorporated herein, and are further illustrated in the Synthesis Examples below.

The compounds of formula I can be used in the form of mixtures with one another and/or with other liquid crystal components such as for example with substances from the classes of Schiff's bases, azobenzenes, azoxybenzenes, phenylbenzoates, cyclohexanecarboxylic acid phenyl esters, cyclohexanecarboxylic acid cyclohexyl esters, biphenyls, phenylcyclohexanes, cyclohexylcyclohexanes, phenylpyrimidines, cyclohexylpyrimidines, phenyldioxanes, 2-cyclohexyl-1-phenylethanes, terphenyls, cyclohexylbiphenyls, cyclohexylphenylpyrimidines and the like. Such substances are known to the person skilled in the art and many of them are, moreover, commercially available.

The liquid crystalline mixtures in accordance with the invention contain at least two components, of which at least one component is a compound of formula I. A second component and optionally further components can be further compounds of formula I or other liquid crystal components. The compounds of formula I are especially suitable for nematic mixtures or, insofar as at least one component of the mixture is optically active, also for cholesteric mixtures.

Having regard to the good solubility of the compounds of formula I and having regard to their good miscibility with one another, their amount in the mixtures in accordance with the invention can be relatively high. However, an amount of about 1–30 wt.%, especially about 3–20 wt.%, of compounds of formula I is generally preferred.

The mixtures in accordance with the invention preferably contain in addition to one or more compounds of formula I one or more compounds from the group of compounds of the formula $$R^1-\left(\text{phenyl}\right)_n-\left(\text{phenyl}\right)-\text{CN} \quad \text{III}$$

$$R^2-\left(\text{phenyl}\right)_n-\left(\text{CH=N-N=}\right)-\left(\text{phenyl}\right)-X^1 \quad \text{IV}$$

$$R^3-\left(\text{cyclohexyl}\right)-\left(\text{phenyl}\right)_n-X^2 \quad \text{V}$$

$$R^3-\left(\text{dioxane}\right)-\left(\text{phenyl}\right)-X^2 \quad \text{VI}$$

$$R^3-\left(\text{cyclohexyl}\right)-\left(\text{CH=N-N=}\right)-\left(A^1\right)_n-\text{CN} \quad \text{VII}$$

$$R^3-\left(\text{cyclohexyl}\right)-\left(\text{cyclohexyl}\right)-\text{CN} \quad \text{VIII}$$

$$R^4-\left(A^1\right)-\text{COO}-\left(\text{phenyl}\right)\begin{array}{c}F\\\text{CN}\end{array} \quad \text{IX}$$

$$R^5-\left(A^2\right)-\left(A^1\right)_n-Z^1-\left(\text{phenyl}\right)\begin{array}{c}X^3\\F\end{array} \quad \text{X}$$

$$R^2-\left(A^1\right)_n-\left(\text{C=CH-N=}\right)^Y-\left(\text{phenyl}\right)-R^6 \quad \text{XI}$$

$$R^3-\left(\text{cyclohexyl}\right)-\left(A^1\right)_n-\left(\text{phenyl}\right)-R^7 \quad \text{XII}$$

$$R^3-\left(\text{cyclohexyl}\right)-\left(\text{cyclohexyl}\right)-R^8 \quad \text{XIII}$$

$$R^3-\left(\text{cyclohexyl}\right)-Z^2-\left(\text{phenyl}\right)-\left(\text{cyclohexyl}\right)-R^9 \quad \text{XIV}$$

$$R^3-\left(\text{cyclohexyl}\right)-Z^2-\left(\text{phenyl}\right)-\left(\text{phenyl}\right)-\left(\text{cyclohexyl}\right)-R^9 \quad \text{XV}$$

$$R^3-\left(\text{cyclohexyl}\right)-\left(\text{CH=N-N=}\right)-\left(\text{phenyl}\right)-\left(\text{cyclohexyl}\right)-R^9 \quad \text{XVI}$$

wherein n stand for the number 0 or 1; $R^2$ and $R^6$ each independently are alkyl, 3E-alkenyl or 4-alkenyl; $X^1$ denotes cyano or fluorine; $R^3$ and $R^9$ each independently are alkyl, 1E-alkenyl, 3E-alkenyl or 4-alkenyl; $X^2$ denotes cyano or —NCS; ring $A^1$ is 1.4-phenylene or trans-1,4-cyclohexylene; $R^4$ is alkyl or 4-alkenyl or at a benzene ring $A^1$ and $R^4$ is alkoxy or 3-alkenyloxy; $X^3$ denotes hydrogen or fluorine; $Z^1$ represents a single covalent bond or —COO—; ring $A^2$ is trans-1,4- cyclohexylene or trans-1,3-dioxan-2,5-diyl; $R^5$ is alkyl, 3E-alkenyl, 4-alkenyl or, if $X^3$ denotes hydrogen, $R^5$ also is 1E-alkenyl; Y represents CH or N; $R^7$ is alkyl, 3E-alkenyl, 4-alkenyl, alkoxy, 2E-alkenyloxy or 3-alkenyloxy; $R^8$ is alkyl, 1, E-alkenyl, 3E-alkenyl, 4-alkenyl, alkoxy, 2E-alkenyloxy, 3-alkenyloxy, alkoxymethyl or 2-alkenyloxymethyl; and $Z^2$ represents a single covalent bond, —COO— or —CH$_2$CH$_2$—.

In formula III-XVI residues $R^2$-$R^9$ preferably are straight-chain groups. They preferably have up to 12, particularly up to 7, carbon atoms.

The compounds of formula III-X are polar liquid crystal components with positive dielectric anisotropy. The compounds of formula XI-XVI are non-polar or weakly polar liquid crystal components The compounds of formula XV and XVI are of interest mainly as dopants with low viscosity and high clearing points, which can be used in small amounts (for example up to about 5 wt.%) to raise the clearing point of the mixture, if desired.

The mixtures in accordance with the invention preferably contain in addition to one or more compounds of formula I one or more non-polar or weakly polar components in a total amount of about 15-80 wt.%, especially about 15-55 wt.%. The non-polar or weakly polar components are preferably selected from the groups consisting of the compounds of formula XI-XVI, particularly formula XI-XIV.

Moreover, the mixtures can contain in addition to one or more compounds of formula I one or more further polar components. The total amount of polar components including compounds of formula I preferably is about 20-85 wt.%, especially about 45-85 wt.%. The polar components which may be used in addition to one or more compounds of formula I are preferably selected from the groups consisting of the compounds of formula III-X.

A particularly preferred mixture thus comprises about 45-85 wt.% of polar components selected from formula I and III-X, at least one component being a compound of formula I, and about 15-55 wt.% of one or more non-polar or weakly polar components selected from formula XI-XVI. The polar portion with a total amount of about 45-85 wt.% may preferably be composed of about 1-30 wt.% especially about 3-20 wt.% of one or more compounds of formula I and about 35-75 wt.% of one or more compounds selected from formula III-X, the percentages referring to the total mixture.

The mixtures in accordance with the invention can also contain optically active compounds (for example optically active 4'-alkyl- or 4'-alkoxy-4-biphenylcarbonitriles) and/or dichroic coloring substances (for example azo, azoxy or anthraquinone coloring substances). The amount of compounds is determined by the solubility, the desired pitch, color, extinction and the like. The amount of optically active compounds and dichroic coloring substances generally amounts to in each case a maximum of about 10 wt.% in the total mixture.

The preparation of the mixtures in accordance with the invention and the preparation of the electro-optical devices can be effected in a manner known per se.

The preparation of the compounds of formula I as well as liquid crystalline mixtures containing them are illustrated further by the following Examples. C is a crystalline phase, $S_B$ is a smectic B phase, N is a nematic phase and I is the isotropic phase, $\Delta\epsilon$ denotes the dielectric anisotropy, $\Delta n$ denotes the optical anisotropy, $\eta$ denotes the bulk viscosity and $\gamma_1$ denotes the rotational viscosity. $k_{11}$ and $k_{33}$ are the elastic constants for spray and bend, respectively. $V_{10}$ denotes the voltage for 10% transmission, and $t_{on}$ and $t_{off}$ denote respectively the switching-on time and the switching-off time.

EXAMPLE 1 a) A suspension of 0.688 g of dry ethyltriphenylphosphonium bromide in 10 ml of tert,. butyl methyl ether was treated at room temperature under inert gas with 0.206 g of potassium tert. butylate, and stirred for 1 hour. The mixture was subsequently cooled to 0°-5° C. and treated dropwise within 15 minutes with a solution of 0.307 g of trans-4'-(3,4-difluorophenyl)-[1,1'-bicyclohexyl]-trans-4-carboxaldehyde in 10 ml of tert. butyl methyl ether. The reaction mixture was stirred at 0-5° C. for a further 45 minutes and concentrated. Chromatographic purification on silica gel with hexane gave 0.303 g of 1-[trans-4-(trans-4-propenylcyclohexyl)cyclohexyl ]-3,4-difluorobenzene with an E/Z ratio of 10:89.

b) A mixture of 0.303 g of the obtained 1-[trans-4-(trans-4-propenylcyclohexyl)cyclohexyl]-3, 4-difluorobenzene, 5 ml of toluene, 0.31 ml of 3N hydrochloric acid and 45 mg of sodium benzenesulfinate was stirred at 60°-65° C. for 3 hours. Subsequently, the reaction mixture was cooled to room temperature, poured on to 20 ml of 10% sodium hydrogencarbonate solution, and extracted with diethyl ether. The organic phases were washed with water, dried over sodium sulfate, and concentrated. Chromatographic purification of the crude product (0.314 g with an E/Z ratio of 83:16) with hexane/ethyl acetate (vol. 98:2) on silica gel treated with silver nitrate, and subsequent recrystallization from diethyl ether/methanol yielded 0.126 g of 1-[trans-4-(trans-4-(1E-propenyl)cyclohexyl]-cyclohexyl]-3,4-difluorbenzene as colorless crystals with m.p. (C-S ) 49.0° C., S -N 65.6° C., cl.p. (N-I) 159.7° C.; $\Delta\epsilon$ (149° C)=3.22.

The following compounds can be prepared in an analogous manner:
1-[trans-4-(trans-4-(1E-butenyl)cyclohexyl)cyclohexyl]-3,4-difluorobenzene;
1-[trans-4-(trans-4-(1E-pentenyl)cyclohexyl)cyclohexyl]-3,4-difluorobenzene;
1-[trans-4-(trans-4-(1E-hexenyl)cyclohexyl)cyclohexyl]-3,4-difluorobenzene;
1-[trans-4-(trans-4-(1E-heptenyl)cyclohexyl)cyclohexyl]-3,4-difluorobenzene;
1-[2-[trans-4-(trans-4-(1E-propenyl)cyclohexyl)cyclohexyl]ethyl]-3,4-difluorobenzene;
1-[2-[trans-4-(trans-4-(1E-butenyl)cyclohexyl)cyclohexyl]ethyl]-3,4-difluorobenzene;
1-[2-[trans-4-(trans-4-(1E-pentenyl)cyclohexyl)cyclohexyl]ethyl]-3,4-difluorobenzene:
1-[2-[trans-4-(trans-4-(1E-hexenyl)cyclohexyl)cyclohexyl]ethyl]-3,4-difluorobenzene;
1-[2-[trans-4-(trans-4-(1E-heptenyl)cyclohexyl)cyclohexyl]ethyl]-3,4-difluorobenzene.

EXAMPLE 2

A suspension of 1.340 g of dry methyltriphenylphosphonium bromide in 15 ml of tert. butyl methyl ether was treated at room temperature under inert gas with 0,420 g of potassium tert. butylate, and stirred for 1 hour. The mixture was subsequently cooled to 0°-5° C. and treated dropwise within 15 minutes with a solution of 0.612 g of trans-4'-(3,4-difluorophenyl)-[1,1'-bicyclohexyl ]-trans-4-carboxaldehyde in 15 ml of tert. butyl methyl ether. The reaction mixture was stirred at 0°–5° C. for a further 45 minutes and concentrated. Chromatographic purification on silica gel with hexane, and subsequent recrystallization from diethyl ether/methanol yielded 0.222 g of 1-[trans-4-(trans-4-vinylcyclohexyl)cyclohexyl]-3,4-difluorobenzene as colorless crystals with m.p. (C-N) 45.2° C., cl.p. (N-I) 108 1° C.

The following compound can be prepared in an analogous manner:

1-[2-[trans-4-(trans-4-vinylcyclohexyl)cyclohexyl]ethyl]-3,4-difluorobenzene.

EXAMPLE 3

Starting Material a) A Grignard solution of 0.706 g of magnesium and 6.0 g of 1-bromo-3.4-difluorobenzene in 14 ml of tetrahydrofuran was treated dropwise at 0° C. within 30 minutes with a solution of 5.55 g of 8-(4-oxocyclohexyl)-1,4-dioxaspiro-[4.5]decane in 23 ml of tetrahydrofuran. The reaction mixture was stirred at room temperature for a further 2 hours Subsequently, the reaction mixture was treated with 39 ml of 10% ammonium chloride solution while cooling and, then, extracted three times with diethyl ether. The organic phases where washed twice with 10% sodium chloride solution, dried over sodium sulfate, filtered and concentrated. There were thus obtained 7.8 g of crude 1-(3,4-difluorophenyl)-4-(1,4-dioxa-8-spiro[4.5]decyl)cyclohexanol.

b) A mixture of 7.8 g of crude 1-(3,4-difluorophenyl)-4-(1,4-dioxa-8-spiro[4.5]decyl) cyclohexanol, 1.05 ml of ethylene glycol, 1.05 g of Amberlyst ® 15 (strongly acid ion exchange resin, Fluka AG) and 80 ml of ethylene chloride was refluxed through neutral aluminum oxide for 3 hours. Subsequently, the mixture was cooled to room temperature and washed twice with water. The aqueous phases were extracted twice with methylene chloride. The organic phases where dried over sodium sulfate, filtered and concentrated. Chromatographic purification of the residue on silica gel with hexane/ethyl acetate (vol. 96:4) gave 4,9 g of 8-[4-(3,4-difluorophenyl)-3-cyclohexenyl]-1,4-dioxaspiro [4.5]decane as colorless crystals.

c) A solution of 4.9 g of 8-[4-(3,4-difluorophenyl)-3-cyclohexenyl]-1.4-dioxaspiro[4.5]decane in 670 ml of ethanol was hydrogenated with 1.0 g Raney nickel at 50° C. under normal pressure until the hydrogen uptake came to a standstill. The reaction mixture was filtered and the filtrate was concentrated. Threefold recrystallization of the obtained crude product (5.0 g) from diethyl ether/hexane yielded 2.52 g of 8-[trans-4-(3,4-difluorophenyl)cyclohexyl]-1, 4-dioxaspiro[4.5]decane. The mother liquors were evaporated. Isomerization of the residue (2.2 g) under inert gas with 11 ml of dimethyl sulfoxide and 0.344 g of potassium tert. butylate at 100° C. for 7 hours yielded after twofold recrystallization further 0.7 g of 8-[trans-4-(3,4-difluorophenyl)cyclohexyl]-1,4-dioxaspiro-[4.5]-decane.

d) A mixture of 3.22 g of 8-[trans-4-(3,4-difluorophenyl)cyclohexyl]-1,4-dioxaspiro[4.5]decane, 21 ml of toluene and 10.5 ml of formic acid was stirred at room temperature for 90 minutes. Subsequently, the reaction mixtures was poured on to 200 ml of water and extracted three times with diethyl ether. The organic phases were washed with 10% sodium hydrogencarbonate solution and with water, dried over sodium sulfate, filtered and concentrated. There were thus obtained 3.1 g of trans-4'-(3,4-difluorophenyl)-[1,1'-bicyclohexyl]-4-one as yellowish crystals.

e) A suspension of 5.5 g of dry methoxymethyl-triphenylphosphonium chloride in 33 ml of tert. butyl methyl ether was treated with 3.7 g of potassium tert. butylate at −15° C. under inert gas and, then, the mixture was stirred at −5° C. for 30 minutes. Subsequently, the mixture was treated dropwise at −5° C. within 1 hour with a solution of 3.1 g of trans-4'-(3,4-difluorophenyl)-[1,1'-bicyclohexyl]-4-one in 30 ml of tert. butyl methyl ether. The reaction mixture was left to react at room temperature for a further 90 minutes, then filtered and the filtrate was concentrated. Chromatographic purification of the residue on silica gel with hexane/ethyl acetate (vol. 99:1) gave 2.0 q of trans-4-(3,4-difluorophenyl)-4'-(methoxymethyl-idene)-[1,1'-bicyclohexyl].

f) A solution of 2.0 g of trans-4-(3,4-difluorophenyl)-4'-(methoxymethylidene)-[1,1'-bicycloheyxl] in 10 ml of tetrahydrofuran and 2.5 ml of 3N hydrochloric acid was heated to 90° C. for 30 minutes. Subsequently, the reaction mixture was cooled to room temperature, poured on to 100 ml of water and extracted with methylene chloride. The organic phase was washed with water, dried over sodium sulfate, filtered and concentrated. There were thus obtained 1.9 g of trans-4'-(3,4-difluorophenyl)-[1,1'-bicyclohexyl]-4-carboxaldehyde with a cis/trans ratio of 27:72 as colorless crystals.

g) 4.5 ml of 0.1N methanolic potassium hydroxide solution was cooled to 5° C. and treated, while stirring, with a solution of 0.808 g of the obtained cis/trans-mixture of trans-4'-(3,4-difluorophenyl)-[1,1'-bicyclohexyl ]-4-carboxaldehyde in 4 ml of methanol. The mixture was stirred at 5° C. for 30 minutes, then poured on to 30 ml of ice/water and extracted with diethyl ether. The organic phases were washed with water, dried over sodium sulfate, filtered and concentrated. Two fold recrystallization of the residue from methanol yielded 0.307 g of trans-4'-(3,4-difluorophenyl)-[1,1'-bicyclohexyl]-trans-4-carboxaldehyde as colorless crystals.

EXAMPLE 4

Starting Material a) A solution of 174.2 g of 4-phenylcyclohexanone in 250 ml of methylene chloride was added dropwise to a suspension of 133.3 g of aluminum chloride in 250 ml methylene chloride at 20° C. while cooling and gassing with nitrogen. The mixture was stirred for a further 30 minutes, until a clear solution was obtained. In the meantime, a suspension of 133.3 g of aluminum chloride in 500 ml of methylene chloride was treated with 172 ml of oxalyl chloride while gassing with nitrogen and then, this mixture was treated dropwise at 20°–25° C. within 1 hour with the above solution of the 4-phenylcyclohexanone-aluminium chloride complex. The reaction mixture was stirred for a further 30 minutes, then cooled to 2° C. and added dropwise within 20 minutes while stirring to a solution of 300 g of calcium chloride in 1 l of water. The mixture was stirred at room temperature for a further 1.5 hours and then poured on to 500 ml of ice/water. The organic phase is separated and washed with 500 ml of semi-saturated sodium chloride solution. The aqueous phases were back-extracted twice with 500 ml of methylene chloride each time. The combined organic phase was dried over sodium sulfate, filtered and concentrated. The obtained oily 4-(4-oxocyclohexyl)benzoyl chloride was dissolved in 400 ml of toluene and the solution was added dropwise to a mixture of 150 ml of methanol, 200 ml of pyridine and 1 l of toluene. The reaction mixture was left to stand overnight and then washed successively with water, 3N hydrochloric acid, semi-saturated sodium hydrogencarbonate solution and water, dried over sodium sulfate, filtered and concentrated. Recrystallization of the residue from toluene at −25° C. gave 128 g of pure 4-(4-oxocyclohexyl)benzoic acid methyl ester with m.p. 91°–92° C.

b) A suspension of 236 g of dry methoxymethyltriphenylphosphonium chloride in 900 ml of tetrahydrofuran was treated with 77 g of potassium tert. butylate while gassing with nitrogen. The suspension was stirred for a further 30 minutes, then cooled to 0° C. and treated dropwise within 30 minutes with a solution of 128 g of 4-(4-oxocyclohexyl)benzoic acid methyl ester in 420 ml of tetrahydrofuran. The reaction mixture was stirred at 0° C. for a further 3 hours, then treated with 550 ml of saturated sodium hydrogencarbonate solution and extracted three times with diethyl ether. The organic phases were washed with water, dried over sodium sulfate, filtered and concentrated. The residue was dissolved in 2.5 l of hexane and 0.8 l of methanol/water (vol. 4:1). The hexane phase was washed with 300 ml of methanol/water (4:1), dried over sodium sulfate, filtered and concentrated. There were thus obtained 123 g of 4-[4-(methoxymethylidene)cyclohexyl]benzoic acid methyl ester with m.p. 58° C.

c) A mixture of 123 g of 4-[4-(methoxymethylidene)-cyclohexyl]benzoic acid methyl ester 1000 ml of toluene and 500 ml of formic acid was stirred vigorously at room temperature overnight. The formic acid phase was separated. The toluene phase was washed neutral with water, dried over sodium sulfate, filtered and concentrated. The crude trans/cis-mixture obtained was dissolved in 600 ml of methanol. The solution was added dropwise at 3° C. within 10 minutes to 1.2 l of 0.1N methanolic potassium hydroxide solution while gassing with nitrogen. The reaction mixture was stirred at 3° C. for a further 1 hour, then poured on to ice/water and extracted with diethyl ether. The organic phases were washed neutral with water, dried over sodium sulfate, filtered and concentrated. Recrystallization of the residue from tert. butyl methyl ether yielded 88.5 g of 4-(trans-4-formylcyclohexyl)benzoic acid methyl ester with m.p. 84°–85° C.

d) A solution of 88.5 g of 4-(trans-4-formylcyclohexyl)benzoic acid methyl ester in 700 ml of toluene was treated while stirring with 1.5 ml of 10% (v/v) sulfuric acid and heated to boiling for 1 hour, with damp toluene being distilled off and being replaced by the addition of fresh toluene. Subsequently, the reaction solution was treated with 1 ml of triethylamine. The mixture was washed three times with 150 ml of water each time, dried over sodium sulfate, filtered and concentrated. Twofold recrystallization of the residue from tert. butyl methyl ether at −25° C. gave 75.4 g of pure 4-[trans-4-(1,3-dioxolan-2-yl) cyclohexyl]benzoic acid methyl ester with m.p. 110°–111° C.

e) A mixture of 100 g 4-[trans-4-(1.3-dioxolan-2-yl)cyclohexyl]benzoic acid methyl ester, 10 g of 5% rhodium/aluminum oxide, 1000 ml of methanol and 1 ml of triethylamine was hydrogenated at 60° C. and under 10 bar of hydrogen, until the hydrogen uptake came to a standstill. The mixture was filtered and the filtrate was concentrated. There were thus obtained 97 g of trans-4-(1,3-dioxolan-2-yl)-[1,1'-bicyclohexyl]-4-carboxylic acid methyl ester (cis/trans ratio 60:40) which were treated with 19.3 g of methanol and 3.4 ml of 10% sodium hydroxide solution. While stirring and gassing with nitrogen the solvent was distilled off, until a boiling point of 90° C. was reached. Subsequently, the mixture was stirred at this temperature for a further 1.5 hours. The semi-solid mixture obtained was cooled slowly while treating cautiously with methylene chloride (300 ml). Subsequently, the mixture was washed with 150 ml of saturated sodium hydrogencarbonate solution, dried over sodium sulfate, filtered and concentrated. Recrystallization of the residue from 800 ml of hexane gave 80.7 g of pure trans-4'-(1,3-dioxolan-2-yl)[1,1'-bicyclohexyl]-trans-4-carboxylic acid methyl ester with m.p. 126°–127° C.

f) A suspension of 3.4 g of lithium aluminum hydride in 200 ml of absolute diethyl ether was treated dropwise within 2 hours with a solution of 26.7 g of trans-4'-(1,3-dioxolan-2-yl)-[1,1'-bicyclohexyl ]-trans-4-carboxylic acid methyl ester in 500 ml of absolute diethyl ether. The reaction mixture was stirred for a further 2 hours and then poured cautiously on to 25 ml of ice/water and 60 ml of 25% hydrochloric acid. The aqueous phase was separated and extracted with diethyl ether. The combined organic phases were washed neutral with water, dried over sodium sulfate, filtered and concentrated. There were thus obtained 23.7 g of trans-4'-(1,3-dioxolan-2-yl)-[1,1'-bicyclohexyl]-trans-4-carbinol.

g) A suspension of 34.5 g of pyridinum chlorochromate in 150 ml of methylene chloride was treated dropwise within 30 minutes with a solution of 23.7 g of trans-4'-(1,3-dioxolan-2-yl)-[1,1'-bicyclohexyl ]-trans-4-carbinol. The reaction mixture was stirred at room temperature for a further 3 hours, then treated with 500 ml of absolute diethyl ether and decanted from the residue (the residue being washed three times with 100 ml of diethyl ether each time). Filtration and concentration of the solution yielded 19.8 g of trans-4'-(1,3-dioxolan-2-yl)-[1,1'-bicyclohexyl ]-trans-4-carboxalde.

h) A solution of 29.4 g of triphenylphosphine in 200 ml of toluene was treated dropwise with 21.0 g of 3,4-difluorobenzyl bromide. The mixture was heated to 65° C. for 3 hours and then heated to boiling for 2 hours. After cooling to room temperature the precipitate was removed by filtration, washed with toluene and dried in vacuo. The obtained 3,4-difluoro-benzyltriphenylphosphonium bromide (41.5 g) was suspended in 500 ml of diethyl ether. The suspension was treated, while gassing with nitrogen, with 9.5 g of potassium tert. butylate, stirred at room temperature for 30 minutes and then treated dropwise at 2° C. with a solution of 19.8 g of trans-4'-(1,3-dioxolan-2-yl)-[1,1'-bicyclohexyl ]-trans-4-carboxaldehyde in 250 ml of absolute diethyl ether. The reaction mixture was stirred at 2° C. for a further 2.5 hours. Subsequently, the mixture was washed with 500 ml of semi-saturated sodium hydrogencarbonate solution and with 300 ml of water, dried over sodium sulfate, filtered and concentrated. The residue was dissolved in 200 ml of hexane and 120 ml of methanol/water (vol. 4:1). The hexane phase was separated, washed with 40 ml of methanol/water (vol. 4:1), dried over sodium sulfate, filtered and concentrated. Chromatographic purification of the residue on silica gel with hexane/ethyl acetate (vol. 9:1) gives trans-4-(1,3-dioxolan-2-yl)-trans-4'-(3,4-difluorostyryl)-[1, 1'-bicyclohexyl].

i) A solution of 23.9 g of trans-4-(1,3-dioxolan-2-yl)-trans-4'-(3,4-difluorostyryl)-[1,1'-bicyclohexyl] in 1200 ml of dioxane and 2.5 ml of triethylamine was hydrogenated at room temperature and under normal pressure with 2.5 g of 5% palladium/carbon, until the hydrogen uptake comes to a standstill. Filtration of the reaction mixture and concentration of the filtrate gives trans-4-(1,3-dioxolan-2-yl)-trans-4'-(3,4-difluorophenethyl)-[1,1'-bicyclohexyl].

j) A mixture of 12.6 g of trans-4-(1,3-dioxolan-2-yl)-trans-4'-(3,4-difluorophenethyl)-[1,1'-bicyclohexyl], 300 ml of toluene and 50 ml of formic acid was stirred overnight under a nitrogen atmosphere. Subsequently, the formic acid phase was separated. The toluene phase was washed with water and saturated sodium hydrogencarbonate solution, dried over sodium sulfate, filtered and concentrated. The obtained trans-4'-(3,4-difluorophenethyl)-[1,1'-bicyclohexyl]-trans-4-carboxaldehyde was recrystallized from methanol.

EXAMPLE 5

Binary mixture BM-1 set forth hereinafter was prepared and its properties were determined at 22° C. and at a reduced temperature 10° C. below the clearing point. The threshold potential and the response times were measured in a TN cell (low bias tilt) having a plate separation of 8 ?m; the 2,5-fold value of $V_{10}$ was used as the operating potential.

Mixture BM-1

80 mole % 4-(2E-butenyloxy)-1-(trans-4-propylcyclohexyl)benzene, 20 mole % 1-[trans-4-(trans-4-(1E-propenyl)cyclohexyl)cyclohexyl]-3,4-difluorobenzene;

m.p. (C-N) 25° C., cl.p. (N-I) 68.9° C.; $k_{33}/k_{11}$ (22° C.)=1.20, $k_{33}/k_{11}$ (58.9° C.)=1.16; $\Delta\epsilon$ (22° C.)=0.971, $\Delta\epsilon$ (58.9° C.)=0.687; $\Delta n$ (22° C.)=0.109, $\Delta n$ (58.9° C.)=0.084; $\eta$ (22° C.)=15.2 cP, $\eta$ (58.9° C.)=4.6 cP; $\gamma_1$ (22° C.)=85 cP, $\gamma_1$ (58.9° C.)=15.8 cP; $V_{10}$ (22° C.)=5.1 V, $V_{10}$ (58.9° C.)=3.8 V; $t_{on}$ (22° C.)=8.9 ms, $t_{on}$ (58.9° C.)=4.2 ms; $t_{off}$ (22° C.)=15 ms. $t_{off}$ (58.9° C.)=9.4 ms.

The corresponding data for pure 4-(2E-butenyloxy)-1-(trans-4-propylcyclohexyl)benzene are: m.p. (C-N) 42.4° C., cl.p. (N-I) 57.5° C.; $k_{33}/k_{11}$ (47.5° C.)=1.16; $\Delta\epsilon$ (47.5° C.)=−0.268; $\Delta n$ (47.5° C.)=0.089; $\eta$ (22° C.)=13.5 cP, $\eta$ (47.5° C.)=4.7 cP; $\gamma_1$ (22° C.)=86 cP, $\gamma_1$ (47.5° C.)=25 cP.

EXAMPLE 6

The following nematic mixtures were prepared and their electro-optical data were measured at 22° C. in a TN cell (low bias tilt) having a plate separation of 6 μm (for Mixtures A-E, J and K) and of 8 μm (for Mixtures F-I and L-M), respectively. These mixtures are particularly suitable for the following applications: Mixtures A-E for TFT applications. Mixtures F-I for STN cells with low multiplexibility and/or for outdoor applications, Mixtures J and K for OMI cells, and Mixtures L-O for STN cells.

Mixture A 10.7 wt.% trans-4-(trans-4-vinylcyclohexyl)cyclohexanecarbonitrile,
9.0 wt.% trans-4-[trans-4-(1E-propenyl)cyclohexyl]cyclohexanecarbonitrile,
8.5 wt.% 5-(3-butenyl)-2-(4-fluorophenyl)-1,3-dioxane,
6.0 wt.% 1-[trans-4-(trans-4-vinylcyclohexyl)cyclohexyl]-4-fluorobenzene,
4.5 wt.% 1-[trans-4-(trans-4-(1E-propenyl)cyclohexyl)cyclohexyl]-4-fluorobenzene,
0 6.0 wt.% trans-5-(1E-propenyl)-2-[trans-4-(4-fluorophenyl)cyclohexyl]-1,3-dioxane,
4.5 wt.% trans-4-[trans-4-(3-butenyl)cyclohexyl]cyclohexanecarboxylic acid 4-fluorophenyl ester,
2.5 wt.% 4-ethyl-1-[trans-4-(4-pentenyl)cyclohexyl]benzene,
6.0 wt.% 4-methyl-1-[trans-4-(trans-4-(1E-propenyl)cyclohexyl)cyclohexyl]benzene,
6.0 wt.% 4-methyl-1-[trans-4-(trans-4-(3-butenyl)cyclohexyl)cyclohexyl]benzene,
5.0 wt.% trans-4-(3-butenyl)-1-(trans-4-ethoxycyclohexyl)cyclohexane,
4.0 wt.% trans-4-(4-pentenyl)-1-(trans-4-ethoxycyclohexyl)cyclohexane,
5.5 wt.% trans-4-(1E-propenyl)-1-[trans-4-(methoxymethyl)cyclohexyl]cyclohexane,
7.8 wt.% 4-[2-(trans-4-butylcyclohexyl)ethyl]-1-[trans-4-(4-pentenyl)cyclohexyl]benzene,
5.0 wt.% trans-4-propylcyclohexanecarboxylic acid 4-[trans-4-(3E-pentenyl)cyclohexyl]phenyl ester,
2.0 wt.% 5-(trans-4-pentylcyclohexyl)-2-[4-(trans-4-propylcyclohexyl)phenyl]pyrimidine,
7.0 wt.% 1-[trans-4-(trans-4-(1E-propenyl)cyclohexyl)cyclohexyl]-3,4-difluorobenzene;
m.p. 31 20° C., cl.p. 96° C.; $V_{10}$=2.38 V, $\Delta n$=0.085, $\eta$=20.2 cP.

Mixture B 8.0 wt.% 5-(3-butenyl)-2-(4-fluorophenyl)-1,3-dioxane,
7.0 wt.% trans-4-(4-pentenyl)cyclohexanecarboxylic acid 4-fluorophenyl ester,
6.0 wt.% 1-[trans-4-(trans-4-vinylcyclohexyl)cyclohexyl]-4-fluorobenzene,
5.0 wt.% 1-[trans-4-(trans-4-(1E-propenyl)cyclohexyl)cyclohexyl]-4-fluorobenzene,
4.0 wt.% 1-[trans-4-(trans-4-(3-butenyl)cyclohexyl)cyclohexyl]-4-fluorobenzene,
5.0 wt.% trans-5-(1E-propenyl)-2-[trans-4-(4-fluorophenyl)cyclohexyl]-1,3-dioxane
4.0 wt.% trans-4-[trans-4-(3-butenyl)cyclohexyl]cyclohexanecarboxylic acid 4-fluorophenyl ester,
4.0 wt.% 4-methyl-1-[trans-4-(trans-4-(1E-propenyl)cyclohexyl)cyclohexyl]benzene,
4.0 wt.% 4-methyl-1-[trans-4-(trans-4-(3-butenyl)cyclohexyl)cyclohexyl]benzene,
6.0 wt.% trans-4-vinyl-1-(trans-4-pentylcyclohexyl)cyclohexane,
11.0 wt.% trans-4-(3E-pentenyl)-1-(trans-4-methoxycyclohexyl)cyclohexane,
10.0 wt.% trans-4-(3-butenyl)-1-(trans-4-ethoxycyclohexyl)cyclohexane,
7.0 wt.% trans-4-(4-pentenyl)-1-(trans-4-ethoxycyclohexyl)cyclohexane,
4.0 wt.% 4-[2-(trans-4-butylcyclohexyl)ethyl]-1-[trans-4-(4-pentenyl)cyclohexyl]benzene,
0 7.0 wt.% trans-4-propylcyclohexanecarboxylic acid 4-[trans-4-(3E-pentenyl)cyclohexyl]phenyl ester,
0 8.0 wt.% 1-[trans-4-(trans-4-(1E-propenyl)cyclohexyl)cyclohexyl]-3,4-difluorobenzene;
m.p. −18° C., cl.p. 85° C.; $V_{10}$=2.87 V, $\Delta n$=0.077, $\eta$=14.8 cP.

Mixture C 3.46 wt.% 4-[trans-4-(1E-propenyl)cyclohexyl]benzonitrile,
5.19 wt.% 4-[trans-4-(4-pentenyl)cyclohexyl]benzonitrile, 6.05 wt.% 4-[trans-5-(4-pentenyl)-1,3-dioxan-2-yl]benzonitrile,
10.38 wt.% trans-4-(trans-4-vinylcyclohexyl)cyclohexanecarbonitrile,
8.65 wt.% trans-4-[trans-4-(1E-propenyl)cyclohexyl]cyclohexanecarbonitrile,
8.65 wt.% 5-(3-butenyl)-2-(4-fluorophenyl)-1,3-dioxane,
6.05 wt.% 1-[trans-4-(trans-4-vinylcyclohexyl)cyclohexyl]-4-fluorobenzene,
4.32 wt.% 1-[trans-4-(trans-4-(1E-propenyl)cyclohexyl)cyclohexyl]-4-fluorobenzene,
4.32 wt.% trans-4-[trans-4-(3-butenyl)cyclohexyl]cyclohexanecarboxylic acid 4-fluorophenyl ester,
2.60 wt.% 4-ethyl-1-[trans-4-(4-pentenyl)cyclohexyl]benzene,
6.05 wt.% 4-methyl-1-[trans-4-(trans-4-(1E-propenyl)cyclohexyl)cyclohexyl]benzene,
6.05 wt.% 4-methyl-1-[trans-4-(trans-4-(3-butenyl)cyclohexyl)cyclohexyl]benzene,
4.76 wt.% trans-4-(3-butenyl)-1-(trans-4-ethoxycyclohexyl)cyclohexane,
3.46 wt.% trans-4-(4-pentenyl)-1-(trans-4-ethoxycyclohexyl)cyclohexane,
7.52 wt.% 4-[2-(trans-4-butylcyclohexyl)ethyl]-1-[trans4-(4-pentenyl)cyclohexyl]benzene,
4.32 wt.% trans-4-propylcyclohexanecarboxylic acid 4-[trans-4-(3E-pentenyl)cyclohexyl]phenyl ester,
2.17 wt.% 5-(trans-4-pentylcyclohexyl)-2-[4-(trans-4-propylcyclohexyl)phenyl]pyrimidine,
6.00 wt.% 1-[trans-4-(trans-4-(1E-propenyl)cyclohexyl)cyclohexyl]-3,4-difluorobenzene;
m.p. < −30° C., cl.p. 82° C.; $V_{10}$=1.76 V, $\Delta n$=0.091, $\eta$=21 5 cP.

Mixture D 10.0 wt.% trans-4-(trans-4-vinylcyclohexyl)cyclohexanecarbonitrile,
9.0 wt.% trans-4-[trans-4-(1E-propenyl)cyclohexyl]cyclohexanecarbonitrile,
10.0 wt.% 5-(3-butenyl)-2-(4-fluorophenyl)-1,3-dioxane,
6.0 wt.% 1-[trans-4-(trans-4-vinylcyclohexyl)cyclohexyl]-4-fluorobenzene,
5.0 wt.% 1-[trans-4-(trans-4-(1E-propenyl)cyclohexyl)cyclohexyl]-4-fluorobenzene,
6.0 wt.% trans-5-(1E-propenyl)-2-[trans-4-(4-fluorophenyl)cyclohexyl]-1,3-dioxane,
5.0 wt.% trans-4-[trans-4-(3-butenyl)cyclohexyl]cyclohexanecarboxylic acid 4-fluorophenyl ester,
5.0 wt.% 4-methyl-1-[trans-4-(trans-4-(1E-propenyl)cyclohexyl)cyclohexyl]benzene,
6.0 wt.% 4-methyl-1-[trans-4-(trans-4-(3-butenyl)cyclohexyl)cyclohexyl]benzene,
7.0 wt.% trans-4-vinyl-1-(trans-4-pentylcyclohexyl)cyclohexane,
5.5 wt.% trans-4-(4-pentenyl)-1-(trans-4-ethoxycyclohexyl)cyclohexane,
8.0 wt.% trans-4-(1E-propenyl)-1-[trans-4-(methoxymethyl)cyclohexyl]cyclohexane,
7.5 wt.% 4-[2-(trans-4-butylcyclohexyl)ethyl]-1-[trans-4-(4-pentenyl)cyclohexyl]benzene,
4.0 wt.% trans-4-propylcyclohexanecarboxylic acid 4-[trans-4-(3E-pentenyl)cyclohexyl]phenyl ester,
6.0 wt.% 1-[trans-4-(trans-4-(1E-propenyl)cyclohexyl)cyclohexyl]-3,4-difluorobenzene;
m.p. −15° C., cl.p. 87° C.; $V_{10}$=2.15 V, $\Delta n$=0.081, $\eta$=20.7 cP.

Mixture E 8.0 wt.% trans-4-(trans-4-vinylcyclohexyl)cyclohexanecarbonitrile,
7.0 wt.% trans-4-[trans-4-(1E-propenyl)cyclohexyl]cyclohexanecarbonitrile,
10.0 wt.% 5-(3-butenyl)-2-(4-fluorophenyl)-1,3-dioxane,
6.5 wt.% 1-[trans-4-(trans-4-vinylcyclohexyl)cyclohexyl]-4-fluorobenzene,
4.5 wt.% 1-[trans-4-(trans-4-(1E-propenyl)cyclohexyl)cyclohexyl]-4-fluorobenzene,
3.7 wt.% 1-[trans-4-(trans-4-(3-butenyl)cyclohexyl)cyclohexyl]-4-fluorobenzene,
4.5 wt.% trans-4-[trans-4-(3-butenyl)cyclohexyl]cyclohexanecarboxylic acid 4-fluorophenyl ester,
6.5 wt.% 4-methyl-1-[trans-4-(trans-4-(1E-propenyl)cyclohexyl)cyclohexyl]benzene,
6.5 wt.% 4-methyl-1-[trans-4-(trans-4-(3-butenyl)cyclohexyl)cyclohexyl]benzene,
6.0 wt.% trans-4-(3-butenyl)-1-(trans-4-ethoxycyclohexyl)cyclohexane,
5.0 wt.% trans-4-(4-pentenyl)-1-(trans-4-ethoxycyclohexyl)cyclohexane,
10.0 wt.% trans-4-(1E-propenyl)-1-[trans-4-(methoxymethyl)cyclohexyl]cyclohexane,
4.5 wt.% 4-[2-(trans-4-butylcyclohexyl)ethyl]-1-(trans-4-pentylcyclohexyl)benzene,
8.0 wt.% 4-[2-(trans-4-butylcyclohexyl)ethyl]-1-[trans-4-(4-pentenyl)cyclohexyl]benzene,
2.3 wt.% 5-(trans-4-pentylcyclohexyl)-2-[4-(trans-4-propylcyclohexyl)phenyl]pyrimidine,
7.0 wt.% 1-[trans-4-(trans-4-(1E-propenyl)cyclohexyl)cyclohexyl]-3,4-difluorobenzene;
m.p. −20° C., cl.p. 98° C.; $V_{10}$=2.62 V, $\Delta n$=0.084, $\eta$=17.5 cP.

Mixture F 7.0 wt.% 4-(5-butyl-2-pyrimidinyl)benzonitrile,
7.0 wt.% 4-[trans-4-(1E-propenyl)cyclohexyl]benzonitrile,
9.0 wt.% 4-(trans-4-propylcyclohexyl)phenylisothiocyanate,
5.0 wt.% 4'-[trans-4-(1E-propenyl)cyclohexyl]-4-cyanobiphenyl,
6.0 wt.% 4-[trans-5-(4-pentenyl)-1,3-dioxan-2-yl]benzonitrile,
3.0 wt.% 5-(trans-4-butylcyclohexyl)-2-cyanopyrimidine,
3.0 wt.% 5-(trans-4-pentylcyclohexyl)-2-cyanopyrimidine,
3.0 wt.% trans-4-[5-trans-4-butylcyclohexyl)-2-pyrimidinyl]cyclohexanecarbonitrile,
7.0 wt.% 4-(4-pentenyl)benzoic acid 4-cyano-3-fluorophenyl ester,
8.0 wt.% 4-(3-butenyl)benzoic acid 4-cyano-3-fluorophenyl ester,
5.0 wt.% 1-[trans-4-(trans-4-(3-butenyl)cyclohexyl)cyclohexyl]-4-fluorobenzene,
6.0 wt.% trans-5-(1E-propenyl)-2-[trans-4-(4-fluorophenyl)cyclohexyl]-1,3-dioxane,
5.0 wt.% trans-4-[trans-4-(3-butenyl)cyclohexyl]cyclohexanecarboxylic acid 4-fluorophenyl ester,
0 8.0 wt.% trans-4-(1E-propenyl)-1-[trans-4-(methoxymethyl)cyclohexyl]cyclohexane,
5.0 wt.% 4-[2-(trans-4-butylcyclohexyl)ethyl]-1-[trans-4-(4-pentenyl)cyclohexyl]benzene,
5.0 wt.% trans-4-propylcyclohexanecarboxylic acid 4-[trans-4-(3E-pentenyl)cyclohexyl]phenyl ester, 8.0 wt.% 1-[trans-4-(trans-4-(1E-propenyl)cyclohexyl)-cyclohexyl]-3,4-difluorobenzene;

m.p. < −25° C., cl.p. 82° C.; $V_{10}$=1.22 V, $\Delta n$=0.137, $\eta$=42.2 cP.

Mixture G 7.0 wt.% 4-(5-butyl-2-pyrimidinyl)benzonitrile,
3.0 wt.% 4-(trans-4-vinylcyclohexyl)benzonitrile,
3.0 wt.% 4-[trans-4-(4-pentenyl)cyclohexyl]benzonitrile,
5.0 wt.% 4'-[trans-4-(1E-propenyl)cyclohexyl]-4-cyanobiphenyl,
9.0 wt.% 4-[trans-5-(4-pentenyl)-1,3-dioxan-2-yl]benzonitrile,
2.0 wt.% 5-(trans-4-butylcyclohexyl)-2-cyanopyrimidine,
3.0 wt.% 5-(trans-4-pentylcyclohexyl)-2-cyanopyrimidine,
3.0 wt.% trans-4-[5-(trans-4-butylcyclohexyl)-2-pyrimidinyl]cyclohexanecarbonitrile.
7.0 wt.% 4-(3-butenyloxy)benzoic acid 4-cyano-3-fluorophenyl ester.
4.0 wt.% 5-(3-butenyl)-2-(4-fluorophenyl)-1,3-dioxane,
3.0 wt.% trans-4-(4-pentenyl)cyclohexanecarboxylic acid 4-fluorophenyl ester,
5.0 wt.% 1-[trans-4-(trans-4-(3-butenyl)cyclohexyl)cyclohexyl]-4-fluorobenzene,
4.0 wt.% trans-5-(1E-propenyl)-2-[trans-4-(4-fluorophenyl)cyclohexyl]-1,3-dioxane,
5.0 wt.% trans-4-[trans-4-(3-butenyl)cyclohexyl]cyclohexanecarboxylic acid 4-fluorophenyl ester,
2.0 wt.% 5-(4-butylphenyl)-2-(4-pentylphenyl)pyrimidine,
3.0 wt.% 5-(trans-4-ethylcyclohexyl)-2-(4-pentylphenyl)pyrimidine,
3.0 wt.% 4'-propyl-4-[trans-4-(4-pentenyl)cyclohexyl]biphenyl,
7.0 wt.% trans-4-(4-pentenyl)-1-(trans-4-ethoxycyclohexyl)cyclohexane,
5.0 wt.% 4-[2-(trans-4-butylcyclohexyl)ethyl]-1-[trans-4-(4-pentenyl)cyclohexyl]benzene,
6.0 wt.% trans-4-propylcyclohexanecarboxylic acid 4-[trans-4-(3E-pentenyl)cyclohexyl]phenyl ester,
4.0 wt.% 5-(trans-4-pentylcyclohexyl)-2-[4-(trans-4-propylcyclohexyl)phenyl]pyrimidine,
7.0 wt.% 1-[trans-4-(trans-4-(1E-propenyl)cyclohexyl)cyclohexyl]-3,4-difluorobenzene;

m.p. < −30° C., cl.p. 91° C.; $V_{10}$=1.38 V, $\Delta n$=0.125, $\eta$=43.8 cP.

Mixture H 6.0 wt.% 4-(5-butyl-2-pyrimidinyl)benzonitrile,
5.0 wt.% 4-(trans-4-vinylcyclohexyl)benzonitrile,
5.0 wt.% 4-[trans-5-(4-pentenyl)-1,3-dioxan-2-yl]benzonitrile,
2.0 wt.% 5-(trans-4-butylcyclohexyl)-2-cyanopyrimidine,
3.0 wt.% 5-(trans-4-pentylcyclohexyl)-2-cyanopyrimidine,
3.0 wt.% trans-4-[5-(trans-4-butylcyclohexyl)-2-pyrimidinyl]cyclohexanecarbonitrile.
6.0 wt.% 4-(3-butenyloxy)benzoic acid 4-cyano-3-fluorophenyl ester,
4.0 wt.% 5-(3-butenyl)-2-(4-fluorophenyl)-1,3-dioxane,
5.0 wt.% trans-4-(4-pentenyl)cyclohexanecarboxylic acid 4-fluorophenylester,
6.0 wt.% trans-5-(1E-propenyl)-2-[trans-4-(4-fluorophenyl)cyclohexyl]-1,3-dioxane,
5.0 wt.% trans-4-[trans-4-(3-butenyl)cyclohexyl]cyclohexanecarboxylic acid 4-fluorophenyl ester,
3.0 wt.% 5-(trans-4-ethylcyclohexyl)-2-(4-pentylphenyl)pyrimidine,
3.0 wt.% 4-methyl-1-[trans-4-(trans-4-(1E-propenyl)cyclohexyl)cyclohexyl]benzene,
5.0 wt.% 4-methyl-1-[trans-4-(trans-4-(3-butenyl)cyclohexyl)cyclohexyl]benzene,
5.0 wt.% trans-4-(3E-pentenyl)-1-(trans-4-methoxycyclohexyl)cyclohexane,
7.0 wt.% trans-4-(4-pentenyl)-1-(trans-4-ethoxycyclohexyl)cyclohexane,
5.0 wt.% 4-[2-(trans-4-butylcyclohexyl)ethyl]-1-[trans-4-(4-pentenyl)cyclohexyl]benzene,
8.0 wt.% trans-4-propylcyclohexanecarboxylic acid 4-[trans-4-(3E-pentenyl)cyclohexyl]phenyl ester.
2.0 wt.% 4'-[2-(trans-4-butylcyclohexyl)ethyl]-4-(trans-4-pentylcyclohexyl)biphenyl,
4.0 wt.% 5-(trans-4-pentylcyclohexyl)-2-[4-(trans-4-propylcyclohexyl)phenyl]pyrimidine,
8.0 wt.% 1-[trans-4-(trans-4-(1E-propenyl)cyclohexyl)cyclohexyl]-3,4-difluorobenzene;

m.p. < −30° C., cl.p. 90° C.; $V_{10}$=1.57 V, $\Delta n$=0.111, $\eta$=31.0 cP.

Mixture I 3.0 wt.% 4'-ethyl-4-cyanobiphenyl,
7.0 wt.% 4-(5-butyl-2-pyrimidinyl)benzonitrile,
3.0 wt.% 4-(5-pentyl-2-pyrimidinyl)benzonitrile,
5.0 wt.% 4-(trans-4-vinylcyclohexyl)benzonitrile,
5.0 wt.% 4'-[trans-4-(1E-propenyl)cyclohexyl]-4-cyanobiphenyl,
4.0 wt.% 4'-[trans-4-(3E-pentenyl)cyclohexyl]-4-cyanobiphenyl,
5.0 wt.% 4'-[trans-4-(4-pentenyl)cyclohexyl]-4-cyanobiphenyl,
5.0 wt.% 4-[trans-5-(4-pentenyl)-1,3-dioxan-2-yl]benzonitrile,
7.0 wt.% 4-(3-butenyloxy)benzoic acid 4-cyano-3-fluorophenyl ester,
4.0 wt.% 5-(3-butenyl)-2-(4-fluorophenyl)-1,3-dioxan,
5.0 wt.% trans-4-(4-pentenyl)cyclohexanecarboxylic acid 4-fluorophenyl ester,
5.0 wt.% trans-5-(1E-propenyl)-2-[trans-4-(4-fluorophenyl)cyclohexyl]-1,3-dioxane,
4.0 wt.% 5-(trans-4-ethylcyclohexyl)-2-(4-pentylphenyl)pyrimidine,
3.0 wt.% 4'-propyl-4-[trans-4-(3E-pentenyl)cyclohexyl]biphenyl,
4.0 wt.% 4'-propyl-4-[trans-4-(4-pentenyl)cyclohexyl]biphenyl,
5.0 wt.% trans-4-(3E-pentenyl)-1-(trans-4-methoxycyclohexyl)cyclohexane,
7.0 wt.% trans-4-(4-pentenyl)-1-(trans-4-ethoxycyclohexyl)cyclohexane,
4.0 wt.% 4-[2-(trans-4-butylcyclohexyl)ethyl]-1-[trans-4-(4-pentenyl)cyclohexyl]benzene,
7.0 wt.% trans-4-propylcyclohexanecarboxylic acid 4-[trans-4-(3E-pentenyl)cyclohexyl]phenyl ester,
4.0 wt.% 5-(trans-4-pentylcyclohexyl)-2-[4-(trans-4-propylcyclohexyl)phenyl]pyrimidine,
4.0 wt.% 1-[trans-4-(trans-4-(1E-propenyl)cyclohexyl)cyclohexyl]-3,4-difluorobenzene;

m.p. < −30° C., cl.p. 96° C.; $V_{10}$=1.57 V, $\Delta n$=0.146, $\eta$=43.1 cP.

Mixture J 4.65 wt.% 4-[trans-4-(1E-propenyl)cyclohexyl]benzoic-trile,
5.58 wt.% 4-[trans-4-(4-pentenyl)cyclohexyl]benzoic-trile,
6.51 wt.% 4-[trans-5-(4-pentenyl)-1,3-dioxan-2-yl]benzonitrile,
11.16 wt.% trans-4-(trans-4-vinylcyclohexyl)cyclohexanecarbonitrile,
9.30 wt.% trans-4-[trans-4-(1E-propenyl)cyclohexyl]cyclohexanecarbonitrile,
9.30 wt.% 5-(3-butenyl)-2-(4-fluorophenyl)-1,3-dioxane,
6.51 wt.% 1-[trans-4-(trans-4-vinylcyclohexyl)cyclohexyl]-4-fluorobenzene,
4.65 wt.% 1-[trans-4-(trans-4-(1E-propenyl)cyclohexyl)cyclohexyl]-4-fluorobenzene,
4.65 wt.% trans-4-[trans-4-(3-butenyl)cyclohexyl]cyclohexanecarboxylic acid 4-fluorophenyl ester,
6.51 wt.% 4-methyl-1-[trans-4-(trans-4-(1E-propenyl)cyclohexyl)cyclohexyl]benzene,
6.51 wt.% 4-methyl-1-[trans-4-(trans-4-(3-butenyl)cyclohexyl)cyclohexyl]benzene,
6.51 wt.% trans-4-(3-butenyl)-1-(trans-4-ethoxycyclohexyl)cyclohexane,
3.72 wt.% trans-4-(4-pentenyl)-1-(trans-4-ethoxycyclohexyl)cyclohexane,
4.65 wt.% trans-4-propylcyclohexanecarboxylic acid 4-[trans-4-(3E-pentenyl)cyclohexyl]phenyl ester,
2.79 wt.% 5-(trans-4-pentylcyclohexyl)-2-[4-(trans-4-propylcyclohexyl)phenyl]pyrimidine,
7.00 wt.% 1-[trans-4-(trans-4-(1E-propenyl)cyclohexyl)cyclohexyl]-3,4-difluorobenzene;
m.p. < −20° C., cl.p. 85° C.; $V_{10}$=1.87 V, $\Delta n$=0.094, $\eta$=22.3 cP.

Mixture K 4.65 wt.% 4-[trans-4-(1E-propenyl)cyclohexyl]benzoic-trile,
5.58 wt.% 4-[trans-4-(4-pentenyl)cyclohexyl]benzoic-trile,
6.51 wt.% 4-[trans-5-(4-pentenyl)-1,3-dioxan-2-yl]benzonitrile,
11.16 wt.% trans-4-(trans-4-vinylcyclohexyl)cyclohexanecarbonitrile,
9.30 wt.% trans-4-[trans-4-(1E-propenyl)cyclohexyl]cyclohexanecarbonitrile,
9.30 wt.% 5-(3-butenyl)-2-(4-fluorophenyl)-1,3-dioxane,
6.51 wt.% 1-[trans-4-(trans-4-vinylcyclohexyl)cyclohexyl]-4-fluorobenzene,
4.65 wt.% 1-[trans-4-(trans-4-(1E-propenyl)cyclohexyl)cyclohexyl]-4-fluorobenzene,
4.65 wt.% trans-4-[trans-4-(3-butenyl)cyclohexyl]cyclohexanecarboxylic acid 4-fluorophenyl ester,
5.58 wt.% 4-(2E-butenyloxy)-1-(trans-4-propylcyclohexyl]benzene,
4.65 wt.% 4'-propyl-4-[trans-4-(4-pentenyl)cyclohexyl]biphenyl,
4.65 wt.% 4-methyl-1-[trans-4-(trans-4-(1E-propenyl)cyclohexyl)cyclohexyl]benzene,
4.65 wt.% 4-methyl-1-[trans-4-(trans-4-(3-butenyl)cyclohexyl)cyclohexyl]benzene,
3.72 wt.% trans-4-(4-pentenyl)-1-(trans-4-ethoxycyclohexyl)cyclohexane,
4.65 wt.% trans-4-propylcyclohexanecarboxylic acid 4-[trans-4-(3E-pentenyl)cyclohexyl]phenyl ester,
2.79 wt.% 5-(trans-4-pentylcyclohexyl)-2-[4-(trans-4-propylcyclohexyl)phenyl]pyrimidine,
7.00 wt.% 1-[trans-4-(trans-4-(1E-propenyl)cyclohexyl)cyclohexyl]-3,4-difluorobenzene;
m.p. < −25° C., cl.p. 84° C.; $V_{10}$=1.82 V, $\Delta n$=0.099, $\eta$=25.3 cP.

Mixture L 4.0 wt.% 4-(5-butyl-2-pyrimidinyl)benzonitrile,
2.0 wt.% 4-(5-pentyl-2-pyrimidinyl)benzonitrile,
5.0 wt.% 4-[5-(4-butylphenyl)-2-pyrimidinyl]benzonitrile,
8.0 wt.% 4-(trans-4-vinylcyclohexyl)benzonitrile,
8.0 wt.% 4-[trans-4-(1E-propenyl)cyclohexyl]benzonitrile,
8.0 wt.% 4-(trans-4-propylcyclohexyl)phenyl isothiocyanate,
4.0 wt.% 4'-[trans-4-(1E-propenyl)cyclohexyl]-4-cyanobiphenyl,
3.0 wt.% 4'-[trans-4-(4-pentenyl)cyclohexyl]-4-cyanobiphenyl,
6.0 wt.% 4-[trans-5-(4-pentenyl)-1,3-dioxan-2-yl]benzonitrile,
3.0 wt.% trans-5-(1E-propenyl)-2-[trans-4-(4-fluorophenyl)cyclohexyl]-1,3-dioxane,
3.0 wt.% 5-(4-butylphenyl)-2-(4-pentylphenyl)pyrimidine,
2.0 wt.% 5-(trans-4-ethylcyclohexyl)-2-(4-pentylphenyl)pyrimidine,
3.0 wt.% 4-ethoxy-1-(trans-4-propylcyclohexyl)benzene,
6.0 wt.% 4'-ethyl-4-[trans-4-(3E-pentenyl)cyclohexyl]biphenyl,
6.0 wt.% 4'-propyl-4-[trans-4-(3E-pentenyl)cyclohexyl]biphenyl,
5.0 wt.% 4'-propyl-4-[trans-4-(4-pentenyl)cyclohexyl]biphenyl,
7.0 wt.% trans-4-(3E-pentenyl)-1-(trans-4-methoxycyclohexyl)cyclohexane,
8.0 wt.% trans-4-(1E-propenyl)-1-[trans-4-(methoxymethyl)cyclohexyl]cyclohexane,
2.0 wt.% 5-(trans-4-pentylcyclohexyl)-2-[4-(trans-4-propylcyclohexyl)phenyl]pyrimidine,
7.0 wt.% 1-[trans-4-(trans-4-(1E-propenyl)cyclohexyl)cyclohexyl]-3,4-difluorobenzene;
m.p < −25° C., cl.p, 100° C.; $V_{10}$=1.88 V, $\Delta n$=0.163, $\eta$=24.9 cP.

Mixture M 4.0 wt.% 4-(5-butyl-2-pyrimidinyl)benzonitrile,
4.0 wt.% 4-(5-pentyl-2-pyrimidinyl)benzonitrile,
9.0 wt.% 4-(trans-4-vinylcyclohexyl)benzonitrile,
9.0 wt.% 4-[trans-4-(1E-propenyl)cyclohexyl]benzonitrile,
8.0 wt.% 4-(trans-4-propylcyclohexyl)phenyl isothiocyanate,
4.0 wt.% 4'-[trans-4-(1E-propenyl)cyclohexyl]-4-cyanobiphenyl,
3.0 wt.% 4'-[trans-4-(3E-pentenyl)cyclohexyl]-4-cyanobiphenyl,
3.0 wt.% 4'-[trans-4-(4-pentenyl)cyclohexyl]-4-cyanobiphenyl,
7.0 wt.% 4-[trans-5-(4-pentenyl)-1,3-dioxan-2-yl]benzonitrile,
4.0 wt.% trans-5-(1E-propenyl)-2-[trans-4-(4-fluorophenyl)cyclohexyl]-1,3-dioxane,
2.0 wt.% 4-ethoxy-1-(trans-4-propylcyclohexyl)benzene,
6.0 wt.% 4'-ethyl-4-[trans-4-(3E-pentenyl)cyclohexyl]biphenyl, 6.0 wt.% 4'-propyl-4-[trans-4-(3E-pentenyl)cyclohexyl]biphenyl,
5.0 wt.% 4'-propyl-4-[trans-4-(4-pentenyl)cyclohexyl]biphenyl,
7.0 wt.% trans-4-(3E-pentenyl)-1-(trans-4-methoxycyclohexyl)cyclohexane,
9.0 wt.% trans-4-(1E-propenyl)-1-[trans-4-(methoxymethyl)cyclohexyl]cyclohexane,
3.0 wt.% 5-(trans-4-pentylcyclohexyl)-2-[4-(trans-4-propylcyclohexyl)phenyl]pyrimidine,
7.0 wt.% 1-[trans-4-(trans-4-(1E-propenyl)cyclohexyl)cyclohexyl]-3,4-difluorobenzene;
m.p. < −30° C., cl.p. 94° C.; $V_{10}=1.89$ V, $\Delta n=0.154, \eta=25.2$ cP.

Mixture N 4.0 wt.% 4'-ethyl-4-cyanobiphenyl,
4.0 wt.% 4'-propyl-4-cyanobiphenyl,
9.0 wt.% 4-(trans-4-vinylcyclohexyl)benzonitrile,
9.0 wt.% 4-[trans-4-(1E-propenyl)cyclohexyl]benzonitrile,
8.0 wt.% 4-(trans-4-propylcyclohexyl)phenyl isothiocyanate,
4.0 wt.% 4'-[trans-4-(1E-propenyl)cyclohexyl]-4-cyanobiphenyl,
4.0 wt.% 4'-[trans-4-(3E-pentenyl)cyclohexyl]-4-cyanobiphenyl,
3.0 wt.% 4'-[trans-4-(4-pentenyl)cyclohexyl]-4-cyanobiphenyl,
7.0 wt.% 4-[trans-5-(4-pentenyl)-1,3-dioxan-2-yl]benzonitrile,
4.0 wt.% trans-5-(1E-propenyl)-2-[trans-4-(4-fluorophenyl)cyclohexyl]-1,3-dioxane,
9.0 wt.% 4-ethoxy-1-[trans-4-(3E-pentenyl)cyclohexyl]benzene,
6.0 wt.% 4'-ethyl-4-[trans-4-(3E-pentenyl)cyclohexyl]biphenyl,
6.0 wt.% 4'-propyl-4-[trans-4-(3E-pentenyl)cyclohexyl]biphenyl,
5.0 wt.% 4'-propyl-4-[trans-4-(4-pentenyl)cyclohexyl]biphenyl,
9.0 wt.% trans-4-(1E-propenyl)-1-[trans-4-(methoxymethyl)cyclohexyl]cyclohexane,
2.0 wt.% 4'-[2-(trans-4-butylcyclohexyl)ethyl]-4-(trans-4-pentylcyclohexyl)biphenyl,
7.0 wt.% 1-[trans-4-(trans-4-(1E-propenyl)cyclohexyl)cyclohexyl]-3 4-difluorobenzene,
m.p. < −30° C., cl.p. 94° C.; $V_{10}=2.01$ V. $\Delta n=0.161$, $\eta=25.0$ cP.

Mixture O 6.0 wt.% 4-[trans-4-(1E-propenyl)cyclohexyl]benzonitrile,
12.0 wt.% 4-[trans-4-(1E-butenyl)cyclohexyl]benzonitrile,
9.0 wt.% 4-[trans-4-(3-butenyl)cyclohexyl]benzonitrile,
6.0 wt.% 4-[trans-4-(3E-pentenyl)cyclohexyl]benzonitrile,
9.0 wt.% 4-(trans-4-propylcyclohexyl)phenyl isothiocyanate,
4.0 wt.% 4'-[trans-4-(1E-propenyl)cyclohexyl]-4-cyanobiphenyl,
3.0 wt.% trans-4-(4-pentenyl)cyclohexanecarboxylic acid 4-fluorophenyl ester,
3.0 wt.% 1-[trans-4-(trans-4-(1E-propenyl)cyclohexyl)cyclohexyl]-4-fluorobenzene,
3.0 wt.% trans-5-(1E-propenyl)-2-[trans-4-(4-fluorophenyl)cyclohexyl]-1,3-dioxane,
3.0 wt.% trans-4-[trans-4-(3-butenyl)cyclohexyl]cyclohexanecarboxylic acid 4-fluorophenyl ester,
2.0 wt.% 5-(trans-4-ethylcyclohexyl)-2-(4-pentylphenyl)pyrimidine,
3.0 wt.% 4-methyl-1-[trans-4-(trans-4-(1E-propenyl)cyclohexyl)cyclohexyl]benzene,
2.0 wt.% 4-methyl-1-[trans-4-(trans-4-(3-butenyl)cyclohexyl)cyclohexyl]benzene,
10.0 wt.% trans-4-(4-pentenyl)-1-(trans-4-ethoxycyclohexyl)cyclohexane,
3.0 wt.% 4-[2-(trans-4-butylcyclohexyl)ethyl]-1-(trans-4-pentylcyclohexyl)benzene,
4.0 wt.% 4-[2-(trans-4-butylcyclohexyl)ethyl]-1-[trans-4-(4-pentenyl)cyclohexyl]benzene,
8.0 wt.% trans-4-propylcyclohexanecarboxylic acid 4-[trans-4-(3E-pentenyl)cyclohexyl]phenyl ester,
3.0 wt.% 5-(trans-4-pentylcyclohexyl)-2-[4-(trans-4-propylcyclohexyl)phenyl]pyrimidine,
7.0 wt.% 1-[trans-4-(trans-4-(1E-propenyl)cyclohexyl)cyclohexyl]-3,4-difluorobenzene;
m.p. < −30° C., cl.p. 98° C.; $V_{10}=2.12$ V, $\Delta n=0.129$, $\eta=21.2$ cP.

We claim:
1. A compound of formula

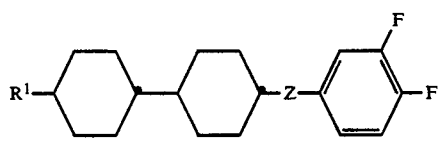

wherein Z is a single covalent bond or —CH₂CH₂—, and $R^1$ is 1E-alkenyl with 2-12 carbon atoms.

2. A compound according to claim 1, wherein $R^1$ is a straight-chain residue.

3. A compound according to claim 1, wherein $R^1$ has 2-7 carbon atoms.

4. A compound according to claim 1, wherein Z is a single covalent bond and $R^1$ is 1E-propenyl.

5. A liquid crystalline mixture having at least 2 components, wherein at least one component is a compound of formula

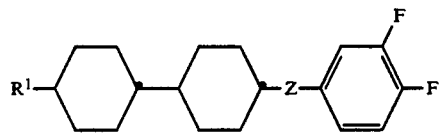

wherein Z is a single covalent bond or —CH₂CH₂—, and $R^1$ is 1E-alkenyl with 2-12 carbon atoms.

6. A liquid crystalline mixture according to claim 5, wherein a compound of formula I in the mixture is present in an amount of 1-30 wt.% of the mixture.

7. A liquid crystalline mixture according to claim 6, wherein the amount of the compound of formula I is 3-20 wt.% of the mixture.

8. A liquid crystalline mixture according to claim 5 comprising one or more compounds of formula I and one or more compounds selected from the group consisting of compounds of the formula

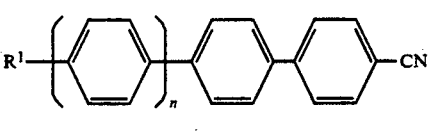

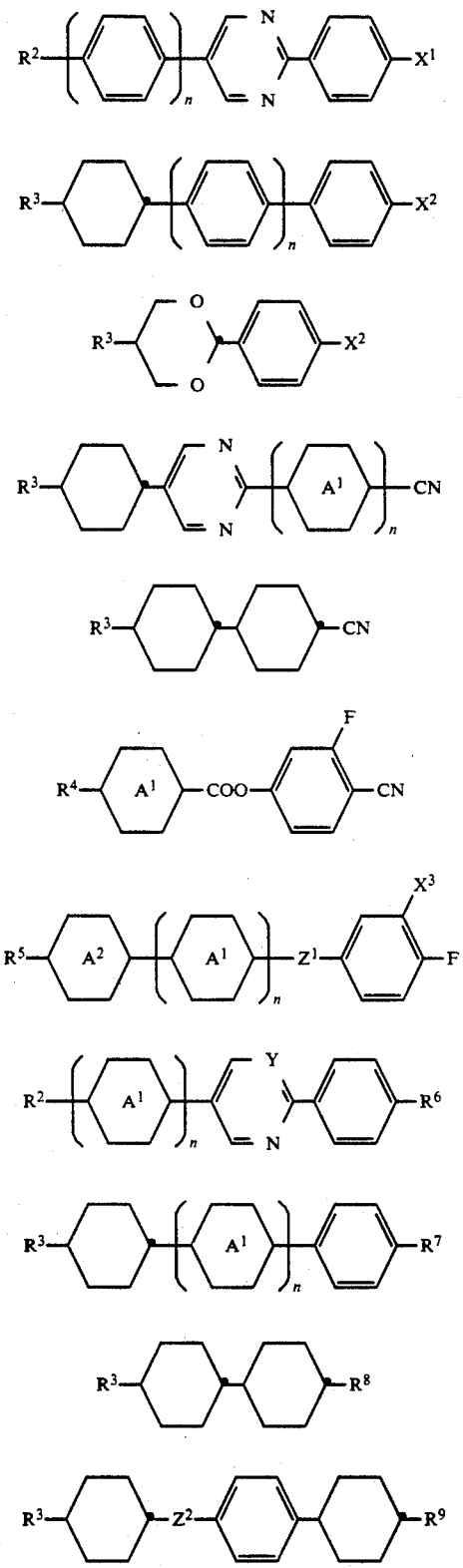

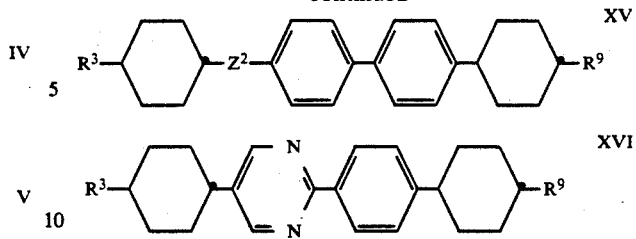

wherein n stand for the number 0 or 1; $R^2$ and $R^6$ each independently are alkyl, 3E-alkenyl or 4-alkenyl; $X^1$ denotes cyano or fluorine; $R^3$ and $R^9$ each independently are alkyl, 1E-alkenyl, 3E-alkenyl or 4-alkenyl; $X^2$ denotes cyano or -NCS; ring $A^1$ is 1,4-phenylene or trans-1,4-cyclohexylene; $R^4$ is alkyl or 4-alkenyl or when A is 1,4-phenylene, $R^4$ is alkoxy or 3-alkenyloxy; $X^3$ is hydrogen or fluorine; $Z^1$ represents a single covalent bond or —COO—; ring $A^2$ is trans-1,4-cyclohexylene or trans-1,3-dioxan-2,5-diyl; $R^5$ is alkyl, 3E-alkenyl, 4-alkenyl or, if $X^3$ is hydrogen, $R^5$ also is 1E-alkenyl; Y represents CH or N; $R^7$ is alkyl, 3E-alkenyl, 4-alkenyl, alkoxy, 2E-alkenyloxy or 3-alkenyloxy; $R^8$ is alkyl, 1E-alkenyl, 3E-alkenyl, 4-alkenyl, alkoxy, 2E-alkenyloxy, 3-alkenyloxy, alkoxymethyl or 2-alkenyloxymethyl; and $Z^2$ represents a single covalent bond, —COO— or —CH$_2$CH$_2$—.

9. A liquid crystalline mixture according to claim 8, comprising one or more compounds of formula I and an amount of 15-80 wt.% of the mixture of one or more compounds selected from the group consisting of compounds of the formula XI-XVI.

10. A liquid crystalline mixture according to claim 9, comprising one or more compounds selected from the group of compounds of formula XI to XVI in an amount of 15-55 wt.% of the mixture.

11. A liquid crystalline mixture according to claim 8, comprising one or more compounds of formula I and one or more compounds selected from the group consisting of compounds of the formula III-X in a total amount of 20-85 wt.% of the mixture.

12. A liquid crystalline mixture according to claim 11 comprising 45 to 85 wt.% of the mixture of compounds of formula I and III-X.

13. In a ferroelectric electro-optical indicating device of the type having a liquid crystalline mixture sandwiched between two transparent plates having polarizers and electrode means, wherein the improvement comprises: said liquid crystalline mixture comprising a compound of formula

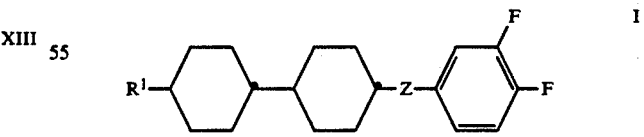

wherein Z is a single covalent bond or —CH$_2$CH$_2$—, and $R^1$ is 1E-alkenyl with 2-12 carbon atoms.

14. A compound according to claim 1, wherein Z is a single covalent bond and $R^1$ is vinyl.

* * * * *